United States Patent
Kendall et al.

(10) Patent No.: US 11,137,339 B2
(45) Date of Patent: Oct. 5, 2021

(54) METHOD FOR PERFORMING A BLOOD COUNT AND DETERMINING THE MORPHOLOGY OF A BLOOD SMEAR

(71) Applicant: Abbott Laboratories, Abbott Park, IL (US)

(72) Inventors: Richard G. Kendall, Miami, FL (US); John W. Roche, Scarborough, ME (US)

(73) Assignee: Abbott Laboratories, Abbott Park, IL (US)

( * ) Notice: Subject to any disclaimer, the term of this patent is extended or adjusted under 35 U.S.C. 154(b) by 5 days.

(21) Appl. No.: 16/657,691

(22) Filed: Oct. 18, 2019

(65) Prior Publication Data
US 2020/0256783 A1    Aug. 13, 2020

Related U.S. Application Data

(63) Continuation of application No. 15/979,236, filed on May 14, 2018, now Pat. No. 10,508,983, which is a
(Continued)

(51) Int. Cl.
*G01N 1/28* (2006.01)
*G01N 15/14* (2006.01)
(Continued)

(52) U.S. Cl.
CPC ....... *G01N 15/1434* (2013.01); *G01N 1/2813* (2013.01); *G01N 15/1475* (2013.01);
(Continued)

(58) Field of Classification Search
CPC ................ G01N 1/2813; G01N 2001/282
See application file for complete search history.

(56) References Cited

U.S. PATENT DOCUMENTS 4,097,845 A * 6/1978 Bacus ................ G06K 9/00127
    348/79
4,702,595 A   10/1987 Mutschler et al.
(Continued)

FOREIGN PATENT DOCUMENTS

WO    1999044593    9/1999
WO    2009117664    9/2009

OTHER PUBLICATIONS

Angulo and Flandrin (2003) "Automated detection of working area of peripheral blood smears using mathematical morphology" Analytical cellular pathology 25(1):37-49.
(Continued)

*Primary Examiner* — Jonathan M Hurst
(74) *Attorney, Agent, or Firm* — Edward J. Baba; Bozicevic, Field & Francis LLP

(57) ABSTRACT

A method for counting blood cells in a sample of whole blood. The method comprises the steps of:
 (a) providing a sample of whole blood;
 (b) depositing the sample of whole blood onto a slide, e.g., a microscope slide;
 (c) employing a spreader to create a blood smear;
 (d) allowing the blood smear to dry on the slide;
 (e) measuring absorption or reflectance of light attributable to the hemoglobin in the red blood cells in the blood smear on the slide;
 (f) recording a magnified two-dimensional digital image of the area of analysis identified by the measurement in step (e) as being of suitable thickness for analysis; and
 (g) collecting, analyzing, and storing data from the magnified two-dimensional digital image.
Optionally, steps of fixing and staining of blood cells on the slide can be employed in the method.

10 Claims, 9 Drawing Sheets

Related U.S. Application Data continuation of application No. 15/044,638, filed on Feb. 16, 2016, now Pat. No. 9,976,945, which is a continuation of application No. 14/299,855, filed on Jun. 9, 2014, now Pat. No. 9,274,054, which is a continuation of application No. 12/644,410, filed on Dec. 22, 2009, now Pat. No. 8,748,186.

(51) Int. Cl.
  *G01N 33/72* (2006.01)
  *G01N 21/59* (2006.01)
  *G01N 21/27* (2006.01)
  *G01N 21/49* (2006.01)
  *G01N 15/00* (2006.01)

(52) U.S. Cl.
  CPC ............ *G01N 21/27* (2013.01); *G01N 21/49* (2013.01); *G01N 21/59* (2013.01); *G01N 33/721* (2013.01); *G01N 2001/282* (2013.01); *G01N 2015/008* (2013.01); *G01N 2015/0073* (2013.01); *G01N 2015/1486* (2013.01); *G01N 2333/805* (2013.01)

(56) References Cited

U.S. PATENT DOCUMENTS

| | | | | |
|---|---|---|---|---|
| 5,352,613 | A | * | 10/1994 | Tafas ........................ C12Q 1/42 435/40.5 |
| 6,151,405 | A | * | 11/2000 | Douglass ............ G01N 15/1475 356/39 |
| 6,235,536 | B1 | | 5/2001 | Wardlow |
| 2009/0238438 | A1 | | 9/2009 | Wardlaw et al. |
| 2009/0257632 | A1 | * | 10/2009 | Lalpuria ................ G01N 15/05 382/128 |
| 2009/0269799 | A1 | | 10/2009 | Winkleman et al. |

OTHER PUBLICATIONS

Bolshakova G. D., "Now peripheral blood smears preparation doesn't depend on laboratory technician's mastery", Scientific and practical magazine, Clinical laboratory consultation, Feb. 2005, No. 6, 2 pages.
CellaVision® DM96 [online]. CellaVision AB 2009, [retrieved on May 12, 2010]. Retrieved from the Internet: <URL: http://www.cellavision.com/?sid=459>, 2 pages.
Christopher Mary M., Evaluation of the Blood Smear [online], 2009, [retrieved on Nov. 25, 2009]. Retrieved from the Internet: <URL: http://www.vin.com/proceedings/Proceedings.pix?CID=WSAVA2004&PID=8610&0=G>, 4 pages.
Digital pathology—Wikipedia, the free encyclopedia [online], [retrieved on Dec. 17, 2009]. Retrieved from the Internet: <URL: http://en.wikipedia.org/wiki/Digital_pathology>, 3 pages.
Fulton Wayne, A few scanning tips [online] 1997-2010, [retrieved on May 12, 2010]. Retrieved from the Internet: <URL: http://www.scantips.com/>. 4 pages.
Hematology Laboratory; Proper preparation of a Peripheral Blood Smear Slide Staining with Wright's Stain [online], [retrieved on Nov. 25, 2009]. Retrieved from the Internet: <URL: cls.umc.edu/COURSES/CLS312/bloodsm.doc>, 5 pages.
Lynch Edward C., "Peripheral Blood Smear", Clinical Methods, The History, Physical and Laboratory Examinations, Third Edition, Kenneth Walker H., Dallas Hall W., Willis Hurst J. (eds), Butterworth Publishers [online], 1990, [retrieved on Nov. 25, 2009]. Retrieved from the Internet: <URL: http://www.ncbi.nlm.nih.gov/bookshelf/br.fcai?book=cm&oart=A4584>, 6 pages.
Microscope—Wikipedia, the free encyclopedia [online], [retrieved on Dec. 16, 2009]. Retrieved from the Internet: <URL: http://en.wikipedia.org/wiki/Microscope>, 5 pages.
Microscopy—Wikipedia, the free encyclopedia [online], [retrieved on Dec. 16, 2009]. Retrieved from the Internet: <URL: http://en.wikipedia.org/wiki/Microscopy>, 17 pages.
Nowakowski G. S., et al., "Percentage of Smudge Cells on Routine Blood Smear Predicts Survival in Chronic Lymphocytic Leukemia", Journal of Clinical Oncology, Apr. 10, 2009, 27 (11), 1844-1849.
Oil immersion—Wikipedia, the free encyclopedia [online], [retrieved on Dec. 22, 2009]. Retrieved from the Internet: <URL: http://en.wikipedia.org/wiki/Oil_immersion_objective>, 3 pages.
Tagliasacchi Daniela et al., Let's Observe the Blood Cells [online], Apr. 1997, [retrieved on Apr. 20, 2010]. Retrieved from the Internet: <URL: http://www.funsci.com/fun3_en/blood/blood.htm>, 12 pages.
The Aperio Digital Pathology Environment [online], Aperio Technologies, Inc., 2001-2010, [retrieved on Apr. 21, 2010]. Retrieved from the Internet: <URL: http://www.aperio.com/pathology-services/index-solutions-software.asp>, 2 pages.
Xiong W. et al., "Automatic Working Area Classification in Peripheral Blood Smears Using Spatial Distribution Features Across Scales", IEEE Xplore—Pattern Recognition, 2008, ICPR 2008, 19th International Conference on [online]. Dec. 8-11, 2008 [retrieved on May 12, 2010]. Retrieved from the Internet: <URL: http://ieeexplore.ieee.org/xpl/mostRecentIssue.jsp?punumber+4740202>., pp. 1-4.
Angulo, et al., Automated detection of working area of peripheral blood smears using mathematical morphology, Analytical Cellular Pathology, 2003, vol. 25, No. 1, pp. 37-49.
Xiong, et al., Automatic Working Area Classification in Peripheral Blood Smears without Cell Central Zone Extraction, Engineering In Medicine and Biology Society, 2008, 30th Annual International Conference of the IEEE, IEEE, USA pp. 4074-4077.

* cited by examiner

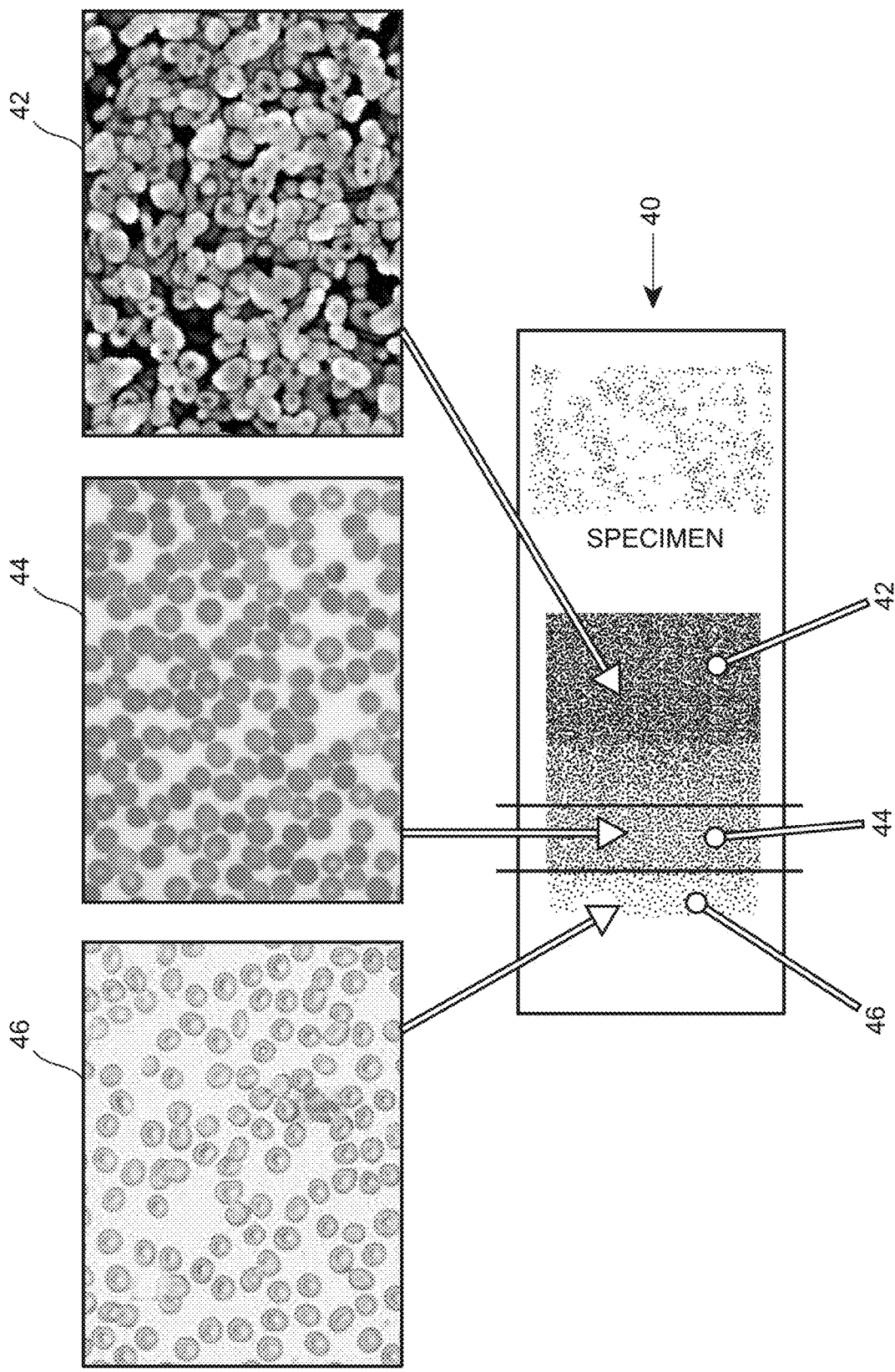

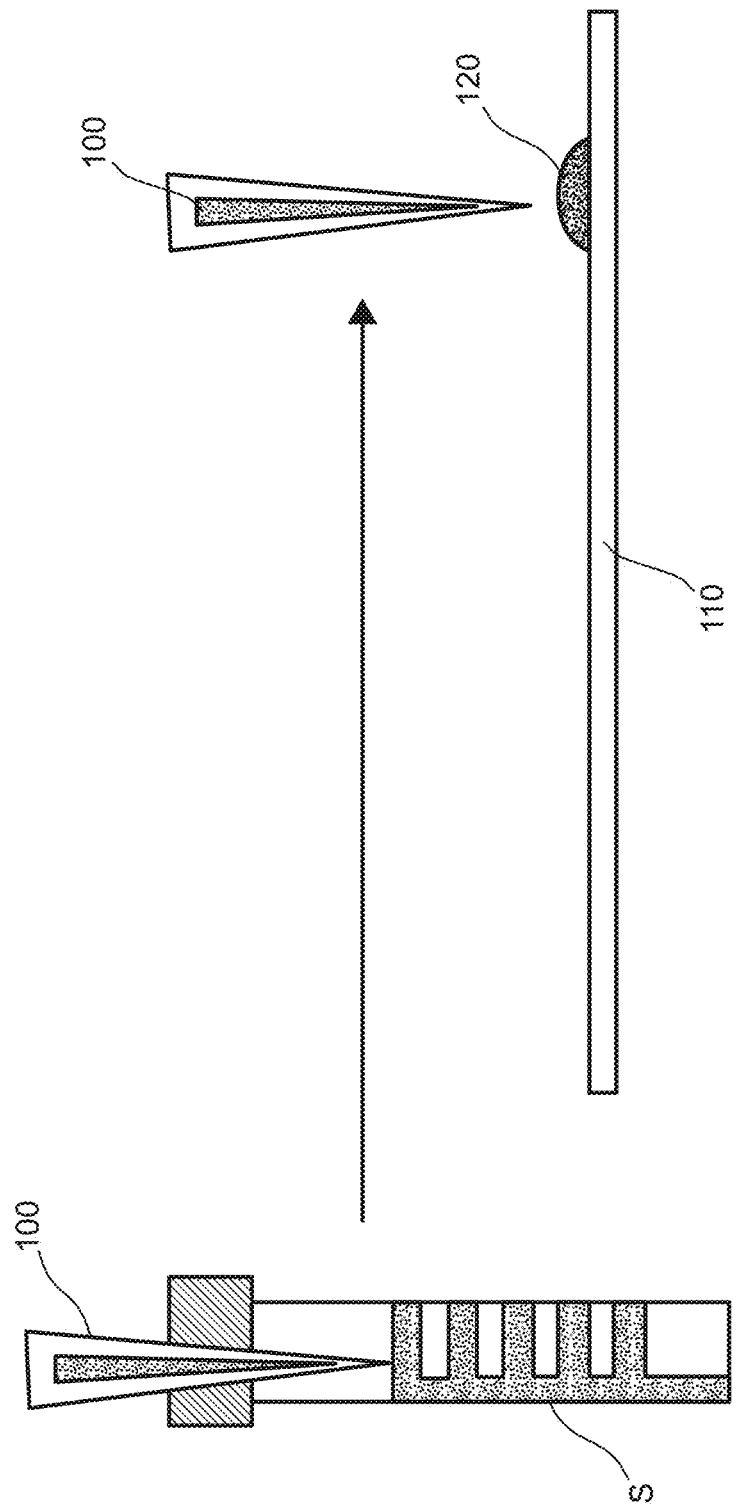

FIG. 8A
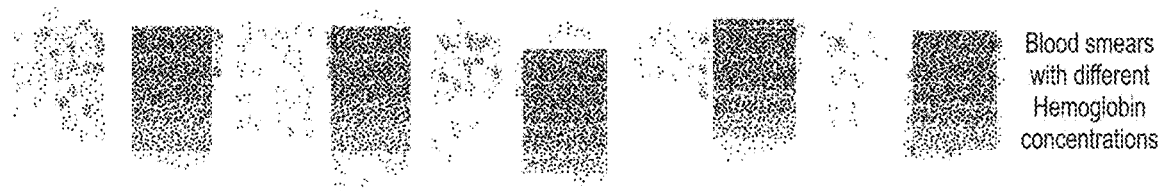
Blood smears with different Hemoglobin concentrations
FIG. 8B
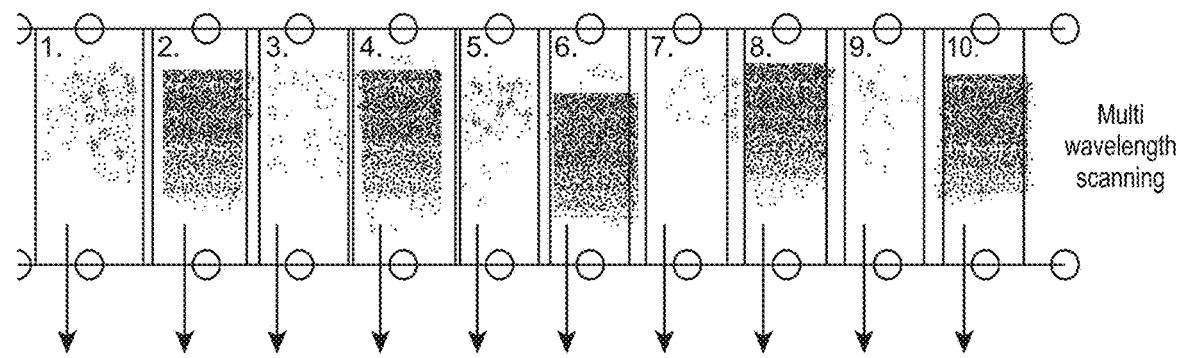
Multi wavelength scanning
FIG. 8C
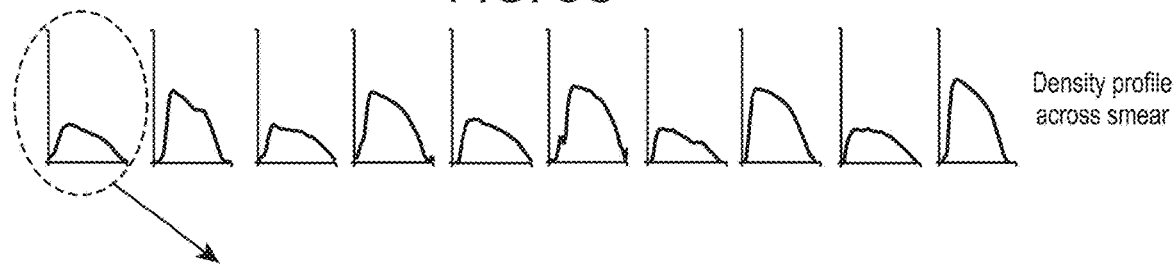
Density profile across smear
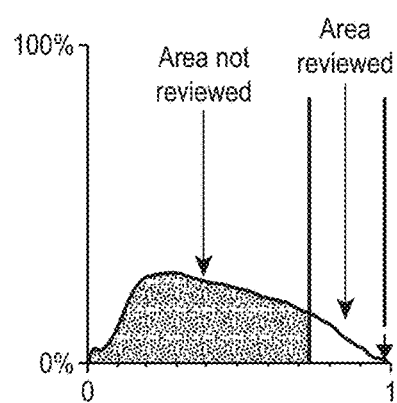
FIG. 8D

METHOD FOR PERFORMING A BLOOD COUNT AND DETERMINING THE MORPHOLOGY OF A BLOOD SMEAR

BACKGROUND OF THE INVENTION

1. Field of the Invention

This invention relates to a method for performing a blood count by means of a blood smear.

2. Discussion of the Art

Automated counting of blood cells typically involves counting blood cells after a sample of whole blood having a known volume is obtained and subsequently diluted in an appropriate diluent. Knowledge of the initial volume of the sample and the degree of subsequent dilution allows a quantitative determination of the numbers of different types of cells in the given volume of the original sample of whole blood. For example, if a microliter of whole blood is diluted so as to yield a volume of 1000 microliters, the dilution ratio is said to be 1:1000, and the dilution factor is said to be 1000. If a blood count for this diluted sample of blood indicates that there are 5000 red blood cells per microliter, the red blood cell count in the original undiluted blood sample is equal to the product of 1000 and 5000, i.e., 5,000,000. Thus, the actual blood count of the undiluted sample is 5,000,000 red blood cells per microliter.

Several physical methods for detecting and enumerating blood cells have been employed, such as, for example, analysis of the impedance characteristics of the blood cells by means of either direct current or radio frequency signals, the use of optical flow cytometry, wherein cells, which are either stained or in their near native state, are examined by means of light scatter characteristics, absorbance characteristics, fluorescence characteristics, or any combination of the foregoing. It has also been suggested that blood cells can be quantified by means of direct imaging of the blood cells in combination with analysis of microscopic images of the blood cells via flow cytometry or while the blood cells are suspended in a chamber having specified dimensions. Instruments have been developed in which either diluted or undiluted samples of blood can be introduced into a counting chamber, the dimensions of which are known, and a blood count can be generated by analysis of digital images. All of these approaches can be used to generate the parameters of a blood count.

After a blood count has been completed by one of the aforementioned methods, a number of the blood samples typically require additional analysis by means of a process that involves preparation, staining, and examination of a blood smear. The process of analyzing a blood smear can employ a variety of techniques, including manual, automated, or semi-automated techniques. The analysis of a blood smear can be used to confirm the accuracy of a blood count, to detect potential interfering substances, and to detect some of the fine sub-cellular features of cells that cannot be detected or interpreted by conventional analyses of a blood count.

Blood cells are not homogeneous. Blood cells contain sub-cellular features that are smaller than the cells themselves. Such sub-cellular features include nuclei, nucleoli, granules, and cell membranes. Particular examples of analyses of sub-cellular features include examination of the shapes of the red blood cells and variations in the shapes of the red blood cells. For example, it is possible to determine the ratio of the size of the nucleus of the cell to the size of the cell itself by measuring the cross sectional area of each (i.e., the nucleus of the cell and the cell itself) and dividing the measured values. This ratio, and various other parameters, can be used to determine the degree of normality of a blood cell.

Potential interfering substances include, but are not limited to, sickle cells, lyse-resistant red blood cells, cells that aggregate for various reasons, nucleated red blood cells, and unusually high lipid concentrations. Generally, these interfering substances are abnormalities in the structure(s) of blood constituent(s), which abnormalities alter the normal reflective and absorptive characteristics of blood constituents, which normal characteristics enable the measurements of blood parameters.

With respect to analysis of a blood smear, after a blood smear is prepared, the blood smear can be stained by means of at least one appropriate stain to identify the morphological characteristics of the blood cells and sub-cellular features of the blood cells. The process of identification can be manual or automated. Typically, a stained blood smear is examined by a human morphologist, who subjectively assesses the morphological appearances of the cells to provide either quantitative impressions of the proportions of different leukocytes or semi-quantitative impressions of the degree of morphological abnormality. Attempts have also been made to automate the process of analyzing a blood smear by means of automated microscopes and software to recognize patterns in digital images to not only classify leukocytes but to also provide an interpretation of the morphological changes.

Thus, the performance of a blood count and the subsequent morphological analysis of a blood sample require discrete steps that may involve processing the sample of blood through an automated blood counting device, forming and staining of a blood smear of the blood sample, either manually or by means of an automated device, followed by morphological review of the stained blood smear, either manually or by means of an automated device.

Although the practices previously described are in widespread use, and although the semi-quantitative assessment of cells is possible by a morphological review, performing a quantitative complete blood count on a blood smear has never been suggested. Such a process has two inherent limitations. When a sample of blood is spread to form a blood smear, the volume of blood used to form the blood smear cannot be sufficiently controlled to a point where an accurate estimate of the volume of blood can be made, with the result that the absolute number of cells present in the blood smear cannot be determined. Furthermore, although devices in which a monolayer of a blood sample can be deposited have been developed, these devices typically rely on centrifugation to distribute cells evenly across the surface of a rectangular-shaped microscope slide. In FIG. 1A, a microscope slide is designated by the reference numeral 10, and a drop of blood is designated by the reference numeral 12a. In FIG. 1B, the microscope slide is designated by the reference numeral 10, and the blood smear is designated by the reference numeral 12b. The arrow 14 represents the direction of rotation of the microscope slide 10 during the centrifugation process. Typically, some unknown volume of the blood sample is lost from the microscope slide during the centrifugation process. Because the quantity of cells lost is unknown and unpredictable, an accurate estimate of the volume of blood remaining on the microscope slide at the end of the analysis cannot be made. Therefore, only limited information can be derived with respect to the proportions of cells in the blood sample, and no information that requires knowledge of the total volume of the blood sample can be made. In effect, no measurements for determining the concentration of cells can be made.

There are two alternative approaches currently used for preparing blood smears. The first approach, which is not in widespread use, is the cover slip method. In this method, a drop of a blood sample is placed on a microscope slide. This drop is covered with a cover slip, and the blood smear is subsequently formed by moving the microscope slide and cover slip in opposite directions, thereby effectively smearing the sample. In FIG. 2A, a microscope slide is designated by the reference numeral 20, a drop of blood is designated by the reference numeral 22a, and a cover slip is designated by the reference numeral 24. In FIG. 2B, the microscope slide is designated by the reference numeral 20, the blood smear is designated by the reference numeral 22b, and the cover slip is designated by the reference numeral 24. The arrow 26 represents the direction of movement of the cover slip 24.

The second approach, which is much more widely used, is the wedge or push smear. In this method, a drop of a blood sample is placed on a first glass slide, typically a microscope slide. A second glass slide, which is termed a smearer or spreader, is first placed downstream of the drop of the blood sample and is then drawn back to the drop of the blood sample, whereby the drop of the blood sample is spread across the line of contact between the drop of the blood sample and the second glass slide. The second glass slide, i.e., the spreader, is then propelled forward, i.e., in the downstream direction, in a single rapid, but gentle, linear motion, whereby the drop of the blood sample is dragged behind the spreader, thereby forming a blood smear. See, for example, Automatic Working Area Classification in Peripheral Blood Smears Using Spatial Distribution features Across Scales, W. Xiong, et al.; LET'S OBSERVE THE BLOOD CELLS, D. Tagliasacchi, et al., April 1997, http://www.funsci.com/fun3_en/blood/blood.htm, incorporated herein by reference. In FIG. 3A, a first glass slide is designated by the reference numeral 30, a drop of blood is designated by the reference numeral 32a, and the second glass slide, i.e., the spreader, is designated by the reference numeral 34. In FIG. 3B, the first glass slide is designated by the reference numeral 30, and the blood smear is designated by the reference numeral 32b. The arrow 36 represents the direction of movement of the second glass slide 34. In the resulting blood smear, the blood sample is deposited on the first glass slide in a wedge in which the thick end of the wedge is positioned at the point of initial contact of the drop of the blood sample on the first glass slide, and the thin end of the wedge, which is positioned downstream of the thick end of the wedge, contains a monolayer of cells. However, the wedge or push smear requires that the morphological analysis be confined to the area of the blood smear in which the cells are distributed very thinly in a true monolayer or in a near monolayer. In FIG. 4, a microscope slide is designated by the reference numeral 40. The thick portion of the blood smear is designated by the reference numeral 42, the thin portion of the blood smear is designated by the reference numeral 44, and the part of the blood smear suitable for counting cells, i.e., the true monolayer or near monolayer, is designated by the reference numeral 46. In the thick portion of the blood smear, the cells may overlay one another to such an extent that an automated instrument or a human morphologist is unable to reliably identify and record the morphology of the cells. Cells distributed in the upper layers tend to occlude the two-dimensional images of the cells in the lower layers, when the cells are viewed from above. To an observer, when the edges of cells overlap, the multiple layers of cells appear as a single large, irregularly shaped area. For example, two-dimensional imaging algorithms have difficulty in discerning the difference between two small overlapping cells and one larger cell having an irregular shape. This problem appears to negate the ability to perform a quantitative analysis of the numbers of leukocytes, erythrocytes, and platelets in a blood smear, because the area of a blood smear that is suitable for cell counting would vary unpredictably from blood sample to blood sample with respect to the thickness and length of the blood smear. Such variations are shown in FIGS. 5A, 5B, 5C, and 5D. In FIG. 5A, the slide is designated by the reference numeral 50a, and the blood smear is designated by the reference numeral 52a; in FIG. 5B, wherein the blood smear exhibits a difference in shape from the blood smear shown in FIG. 5A, the slide is designated by the reference numeral 50b, and the blood smear is designated by the reference numeral 52b; in FIG. 5C, wherein the blood smear exhibits a difference in length from the blood smear shown in FIG. 5A, the slide is designated by the reference numeral 50c, and the blood smear is designated by the reference numeral 52c; in FIG. 5D, wherein the blood smear exhibits a difference in breadth from the blood smear shown in FIG. 5A, the slide is designated by the reference numeral 50d, and the blood smear is designated by the reference numeral 52d. In summary, even if the same volumes of blood samples were used to form blood smears, the areas being evaluated for counting cells would differ from sample to sample. The principal factor for determining the thickness and length of a blood smear would likely be the overall viscosity of the sample, which, in turn, is likely to be determined primarily by the concentration of hemoglobin in the sample.

Additional information relating to methods for examining blood smears can be found at, for example, Peripheral Blood smear—Clinical Methods—NCBI Bookshelf, Clinical methods, The History, Physical, and Laboratory Examinations, Third edition, H. Kenneth Walker, W. Dallas hall, J. Willis Hurst, Butterworths, Peripheral Blood Smear, Edward C. Lynch, http://www.ncbi.nlm.nih.gov/bookshelf/br.fcgi?book=cm&part=A4584; Hematology Laboratory: Proper Preparation of a Peripheral Blood Smear, Slide Staining with Wright's Stain; Now peripheral blood smears preparation doesn't depend on laboratory technician's mastery, Scientific and practical magazine «Clinical laboratory consultation»No. 6, February, 2005: yahoo answers, http://answers.yahoo.com/question/index?qid=2009082403233AAEtfnf; and Evaluation of the Blood Smear, M. Christopher, University of California Davis, Department of Pathology, Microbiology and Immunology School of Veterinary Medicine, Davis Calif., USA, &Print=1&O=Generic, all of which are incorporated herein by reference.

SUMMARY OF THE INVENTION

In one aspect, this invention provides a method for counting blood cells in a sample of whole blood. The method comprises the steps of:

(a) providing a sample of whole blood;
(b) depositing the sample of whole blood onto a slide, e.g., a microscope slide;
(c) employing a spreader to create a blood smear;
(d) allowing the blood smear to dry on the slide;

(e) measuring absorption or reflectance of light attributable to the hemoglobin in the red blood cells in the blood smear on the slide;

(f) recording a magnified two-dimensional digital image of the area of analysis identified by the measurement in step (e) as being of suitable thickness for analysis; and (g) collecting, analyzing, and storing data from the magnified two-dimensional digital image.

Optionally, process steps for fixing and staining of blood cells on the slide can be used in the aforementioned method.

It is preferred that the sample of whole blood be a sample of mixed whole blood. The volume of the sample of whole blood used to form the blood smear can be determined either directly by applying a known volume of the blood sample to the slide, or indirectly by determining the volume of the blood applied to the slide by means of a measurement of optical density or reflectance of the blood smear on the slide and converting the value so obtained to a volumetric measure by means of an independent measurement of hemoglobin made by an instrument, such as, for example, an automated hematology analyzer or a spectrometer.

The concentration of hemoglobin in a sample of whole blood can be determined directly at the point of aspiration, typically by means of reflectance measurement of the blood sample in an optically clear sampling probe, such as, for example, a glass capillary tube. Alternatively, the concentration of hemoglobin in a sample of whole blood can be determined directly by means conventional absorbance measurements following dilution of the sample. In still another alternative, the concentration of hemoglobin in a sample of whole blood can be determined by measuring absorbance or reflectance of light attributable to hemoglobin in the red blood cells in a blood smear on a slide. When the concentration of hemoglobin is known, the blood smear can be scanned by a low power imaging device to determine the optical density of the blood in the blood smear. Because this measurement would effectively determine the amount of hemoglobin in the sample of whole blood used to form the blood smear, the volume of whole blood that was actually aspirated and deposited on the slide can be calculated.

In another aspect, this invention provides a device for counting blood cells in a sample of whole blood. The device comprises:

(a) a holder for presenting a container containing a sample of whole blood to an aspiration/dispensing device, an aspiration/dispensing device for withdrawing a sample of whole blood from the container and depositing the sample of whole blood onto a slide, e.g., a microscope slide;

(b) a spreader for spreading the sample of whole blood across the slide to create a blood smear;

(c) a dryer for drying the blood smear on the slide;

(d) a first imaging system capable of measuring the absorption or reflectance of light on account of the hemoglobin in the red blood cells in the blood smear on the slide;

(e) a second imaging system capable of recording a magnified, two-dimensional digital image of the area of analysis identified by the first imaging system as being of suitable thickness for analysis; and (f) a computer to collect, analyze, and store results of the magnified two-dimensional digital image.

Optionally, the device can employ a positioner for positioning the slide to enable further processing of the blood smear.

The method and the device described herein can consolidate the process of blood counting and review of a blood smear in a single instrument. The method and device described herein require only a few reagents, which reagents are inexpensive. The method and device described herein are not complex in a technological sense, because only a single undiluted volume of whole blood is used.

The method and device described herein can detect abnormalities that are currently undetectable by conventional hematology analyzers. Such abnormalities include abnormal red blood cell associations (Rouleaux and aggregation), red blood cell inclusion bodies such as Howell-Jolly bodies and malarial parasites. The method and device described herein can also show sub-cellular changes in the white blood cells, such as the Auer rods seen in acute myeloid leukemias or nucleoli seen in blast cells. Finally, the method and device described herein can detect plasma abnormalities, such as, for example, increases in protein levels, which can be seen in cases of paraproteinemia.

The analysis of the blood count and the blood smear can be performed on the same sample of whole blood, thereby giving the user the opportunity to directly review the instrument's interpretation of the classification of cells.

BRIEF DESCRIPTION OF THE DRAWINGS

FIG. 1A is a top plan view of a slide showing a drop of whole blood deposited on the slide prior to centrifugation. FIG. 1B is a top plan view of the slide of FIG. 1A showing a blood smear formed by means of the centrifugation method.

FIG. 2A is a top plan view of a slide showing a drop of whole blood deposited on the slide prior to formation of a blood smear. FIG. 2B is a top plan view of the slide of FIG. 2A showing a blood smear formed by means of the cover slip method.

FIG. 3A is a side view in elevation of a slide showing a drop of whole blood deposited on the slide prior to formation of a blood smear. FIG. 3B is a top plan view of the slide of FIG. 3A showing a blood smear formed by means of the wedge or push method.

FIG. 4 is a top plan view of a slide illustrating a blood smear exhibiting a wedge, wherein the wedge has three different regions, in which the blood smear in one region is thicker than desired, the blood smear in a second region is thinner than desired, and the blood smear in a third region is actually desired for morphological review.

FIG. 7 is a schematic diagram illustrating the dispensing of a known volume of a sample of whole blood onto a slide.

FIGS. 8A, 8B, 8C, and 8D illustrate how blood smears having different thickness profiles and concentrations of hemoglobin can be scanned by means of low power imaging to establish the volumetric distribution of the blood sample across the blood smear, thereby enabling determination of the volume of blood contained within the area of the blood smear examined for morphology and cell counting. FIGS. 8A and 8B are top plan views of ten (10) slides, each slide having a blood smear formed thereon. FIG. 8C consists of ten (10) graphs, one graph for each slide, illustrating profiles of the blood smears shown in FIGS. 8A and 8B. FIG. 8D is a graph illustrating a profile of a blood smear. The graph in FIG. 8D designates the portion of the blood smear that is eligible for review, i.e., the portion in which blood cells are counted.

DETAILED DESCRIPTION

Figure 1B:
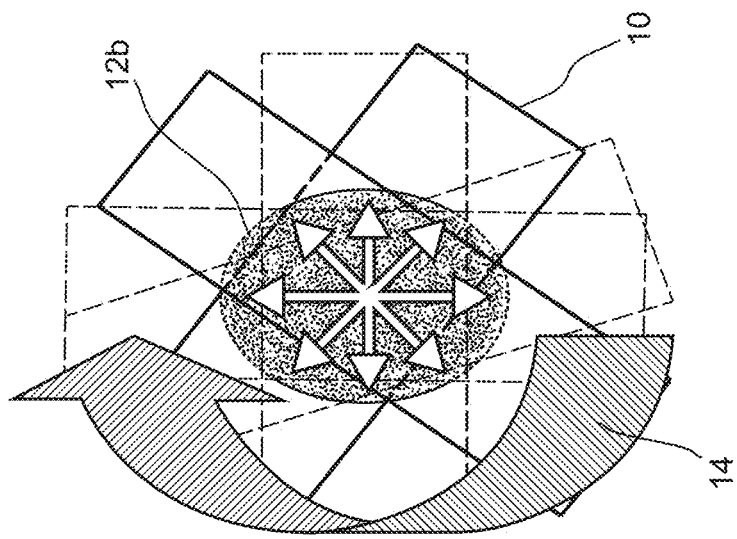
FIGS. 1A and 1B illustrate one method of preparing a blood smear, i.e., a centrifugal method.

As used herein, the expression "whole blood" means a living tissue that circulates through the heart arteries, veins, and capillaries carrying nourishment, electrolytes, hormones, vitamins, antibodies, heat, and oxygen to the body's tissues. Whole blood contains red blood cells, white blood cells, and platelets suspended in a fluid called plasma. As used herein, the expression "sample of blood" is synonymous with the expression "blood sample." As used herein, the expression "sample of whole blood" is synonymous with the expression "whole blood sample." As used herein, the expression "blood smear" means a thin film of blood prepared for the purpose of microscopic image analysis of the individual cells contained therein, usually on a microscope slide, and optionally stained or mixed to impart permanency. As used herein, the expression "sample of mixed whole blood" means a sample of whole blood that has been mixed to resuspend cells in a homogeneous mixture. Blood cells from sample of whole blood drawn directly from a patient, in the absence of further processing, tend to settle over a period of time after being drawn. Accordingly, the sample of whole blood is mixed prior to being tested. As used herein, the expression "complete blood count" means a test requested by a doctor or other medical professional that gives information about the cells in a patient's blood. The cells that circulate in the bloodstream are generally divided into three types: white blood cells (leukocytes), red blood cells (erythrocytes), and platelets (thrombocytes). For additional information, see Complete blood count—Wikipedia, the free encyclopedia, http://en.wikipedia.org/wiki/Complete_blood_count, incorporated herein by reference. As used herein, the term "slide" means a small glass plate for mounting specimens to be examined under a microscope.

As used herein the term "metameter" means a transformed value, in contrast to one that is directly measured. As used herein, the expression "red cell distribution width" is a measure of the health of the red blood cell population according to the distribution of cell sizes. If the cell sizes of a population of red blood cells from a given sample of whole blood are measured and plotted in a histogram with the number of cells of a given size as a function of the size of the cells, the result is the red cell distribution of sizes of the cell, which is approximately a normal distribution. Accordingly, the expression "red cell distribution width" means the quotient of the standard deviation of the distribution of red blood cells divided by the mean of the distribution of red blood cells, usually multiplied by 100% to convert the quotient to a percent (%).

As used herein, the expression "mean corpuscular volume" (MCV) means the average volume of a red blood cell, measured in femtoliters. As used herein, the expression "mean corpuscular hemoglobin concentration" (MCHC) means the average amount of hemoglobin in a given volume of red blood cells, measured in percent (%). As used herein, the expression "concentration of hemoglobin" means the amount of hemoglobin in a volume of blood, measured in g/dL. As used herein, the expression "mean corpuscular hemoglobin" (MCH) means the average amount of hemoglobin in the average red blood cell, measured in picograms.

As used herein, the expression "cytoplasmic ratio" means the ratio of the volume of the cytoplasm in a cell to the total volume of the cell. As used herein, the expression "nuclear ratio" means the ratio of the volume of the nucleus in a cell to the total volume of the cell.

As used herein, the expression "line of contact" refers to the process of forming a wedge or push smear. In order to form this type of blood smear, a drop of a sample of whole blood is placed near an end of a glass slide. A smearer or spreader having a straight edge is touched to the glass slide and pushed into the drop of whole blood, thereby spreading the drop across the line of contact between the smearer or the spreader and the glass slide. Then the direction of the smearer or the spreader is reversed, and the smearer or spreader is pulled along the length of the glass slide, thereby pulling a line of the drop of whole blood with it. The blood is spread on the glass slide in a film until it is depleted, with the result that a wedge of blood remains on the slide. As used herein, the term "wedge" refers to the observation that the film of blood, i.e., the blood smear, is thicker at one end of the slide than it is at the other. Viewed from above, the film of blood, i.e., the blood smear, appears to be a rectangle. However, the rectangle is darker at one end of the glass slide and its color becomes progressively lighter towards the other end of the glass slide as the film of blood, i.e., the blood smear, becomes thinner.

As used herein, the term "absorbance" means optical density. Absorbance is represented by the formula $$A_\lambda = -\log_{10}(I/I_o)$$

where I represents the intensity of light at a specified wavelength $\lambda$ that has passed through a sample (transmitted light intensity) and $I_O$ represents the intensity of the light before it enters the sample or incident light intensity. Absorbance measurements are often carried out in analytical chemistry, because the absorbance of a sample is proportional to the thickness of the sample and the concentration of the absorbing species in the sample, in contrast to the transmittance $I/I_O$ of a sample, which varies logarithmically with thickness and concentration.

As used herein, the term "reflectance" means a measure of the incident electromagnetic radiation that is reflected by a given interface. It is closely related to reflectivity but reflectance is more applicable to thin reflecting objects. Reflectance can vary for thin objects due to variations in the surface thickness and approaches the reflectivity as the surface becomes thicker. The reflectance may be calculated by comparing the amount of reflected radiation to the amount of incident radiation.

As used herein, the expression "low power imaging" and the like refers to imaging wherein a 10× objective lens of a microscope is employed. As used herein, the expression, "high power imaging" and the like refers to imaging wherein a magnification of 40× to 100× is employed. It should be noted that a magnification of 40× does not require oil immersion, while a magnification of 100× preferably employs oil immersion. Oil immersion is a technique used to increase the resolution of a microscope. Increased resolution is achieved by immersing both the objective lens and the specimen in a transparent oil of high refractive index, thereby increasing the numerical aperture of the objective lens. Oil immersion is described in greater detail in Oil immersion—Wikipedia, the free encyclopedia, http://en.wikipedia.org/wiki/Oil_immersion_objective, incorporated herein by reference. It should be noted that when low power imaging is used in the method and apparatus described herein, high resolution is not required, because the purpose of low power imaging is to determine the portion of the slide where cells are to be counted. The portion of the slide where cells are to be counted is a true monolayer or a nearly true monolayer. In contrast, it should be noted that when high power imaging is used in the method and apparatus described herein, a higher resolution than that provided by the low power imaging features is required so that the various types of blood cells can be counted individually. It should also be noted that "low power imaging" is synonymous with relatively low magnification (e.g., 10×) and that "high power imaging" is synonymous with relatively high magnification (e.g., 40× to 100×). Magnifications other than those set forth herein can be used, so long as the high power imaging provides a substantially higher magnification than does the low power imaging, i.e., at least about 4:1, along with adequate resolution. Additional discussion of magnification and other characteristics of microscopes, such as, for example, resolution, can be found in Microscope—Wikipedia, the free encyclopedia, http://en.wikipedia.org/wiki/Microscope, incorporated herein by reference, and Microscopy—Wikipedia, the free encyclopedia, http://en.wikipedia.org/wiki/Microscopy, incorporated herein by reference.

The method described herein comprises the steps of:
(a) providing a sample of whole blood;
(b) depositing the sample of whole blood onto a slide, e.g., a microscope slide;
(c) employing a spreader to create a blood smear;
(d) allowing the blood smear to dry on the slide;
(e) measuring absorption or reflectance of light attributable to the hemoglobin in the red blood cells in the blood smear on the slide;
(f) recording a magnified two-dimensional digital image of the area of analysis identified by the measurement in step (e) as being of suitable thickness for analysis; and
(g) collecting, analyzing, and storing data from the magnified two-dimensional digital image.

Optionally, process steps for fixing and staining of blood cells on the slide can be used in the aforementioned method. Based on the aforementioned method, it follows that a device for carrying out the method comprises:
(a) a holder for presenting a container containing a sample of whole blood to an aspiration/dispensing device, an aspiration/dispensing device for withdrawing a sample of whole blood from the container and depositing the sample of whole blood onto a slide, e.g., a microscope slide;
(b) a spreader for spreading the sample of whole blood across the slide to create a blood smear;
(c) a dryer for drying the blood smear on the slide;
(d) a first imaging system capable of measuring the absorption or reflectance of light on account of the hemoglobin in the red blood cells in the blood smear on the slide;
(e) a second imaging system capable of recording a magnified, two-dimensional digital image of the area of analysis identified by the first imaging system as being of suitable thickness for analysis; and
(f) a computer to collect, analyze, and store results of the magnified two-dimensional digital image.

Optionally, the device can include a positioner for positioning the slide to enable further processing of the blood smear.

The major dimension of the magnified two-dimensional image is typically parallel to the longer edge of the slide and the minor dimension of the magnified two-dimensional image is typically parallel to the shorter edge of the slide.

The blood cells in the blood smear can be stained with, for example, cytochemical stains, such as, for example, Wright's stain, May-Grunwald-Giemsa stain, new methylene blue, Field's stain, peroxidase or fluorescent staining, before or after spreading. In some instances, staining procedures are not required.

If staining is required, the slide can be processed appropriately before being delivered to the imaging component(s) of the device. The imaging component(s) scans the entire slide, or a selected area(s) of the slide, at an appropriate level of magnification for the resolution required to perform the analysis. Imaging component(s) suitable for use herein is (are) described in http://www/aperio.com/pathology-service/index-solutions-software.asp, incorporated herein by reference.

Figure 1A:
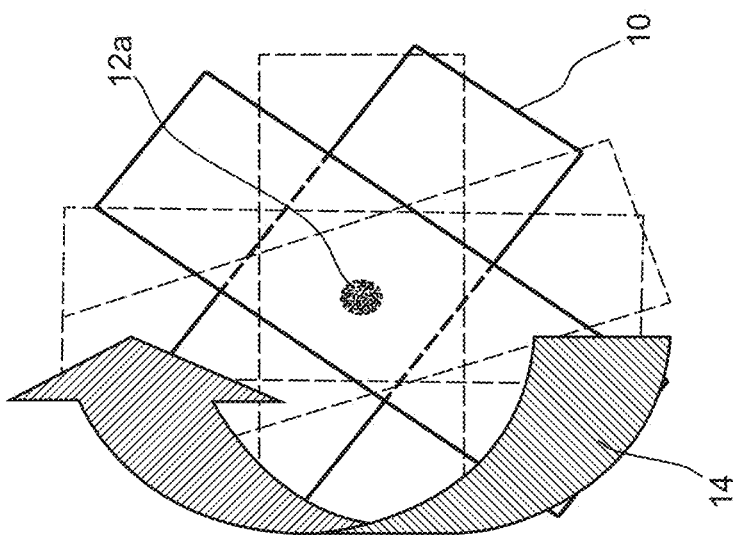
Figure 2A:
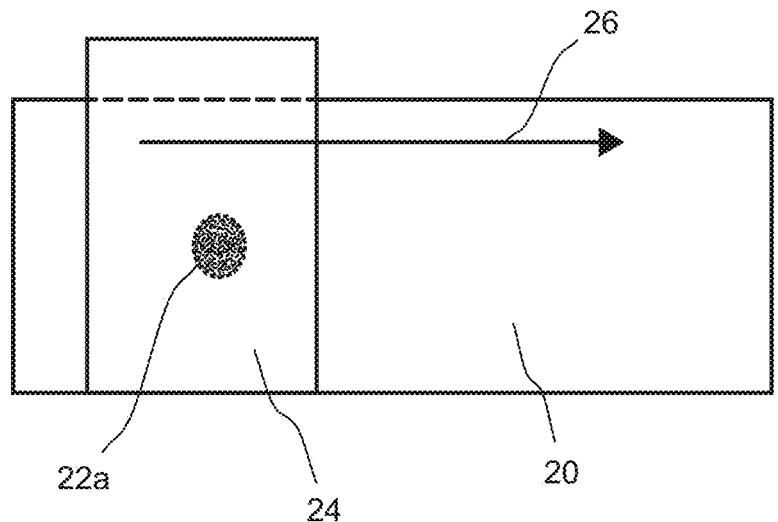
FIGS. 2A and 2B illustrate a second method of preparing a blood smear, i.e., a cover slip method.
Figure 2B:
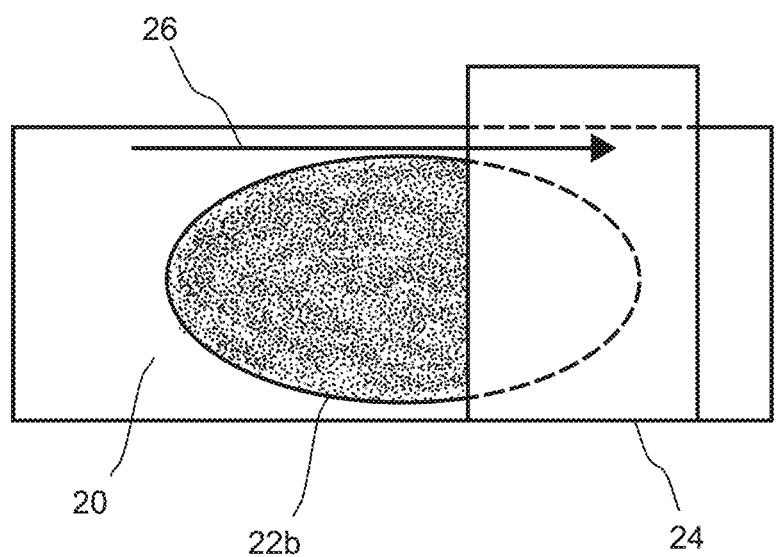
Figure 3A:
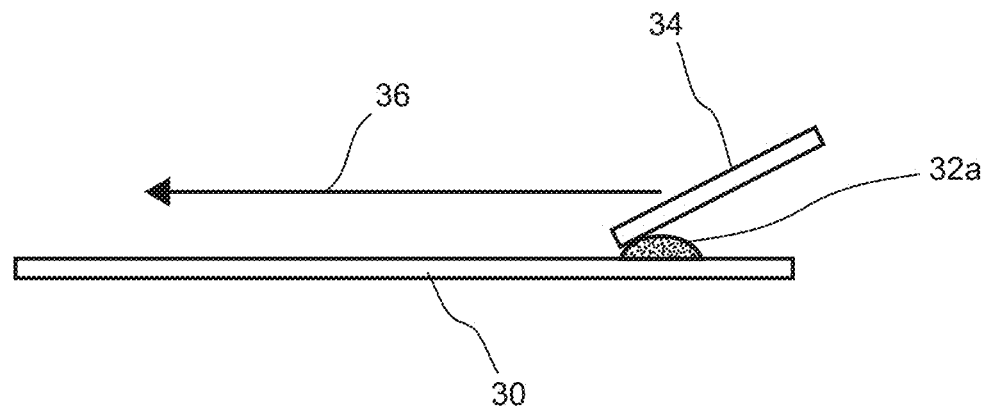
FIGS. 3A and 3B illustrate a third method of preparing a blood smear, i.e., a wedge or push method.
Figure 3B:
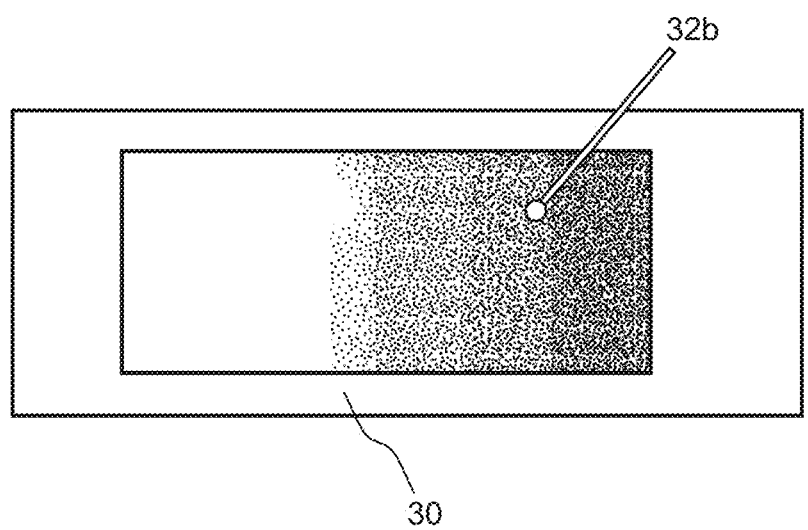
Figure 5B:
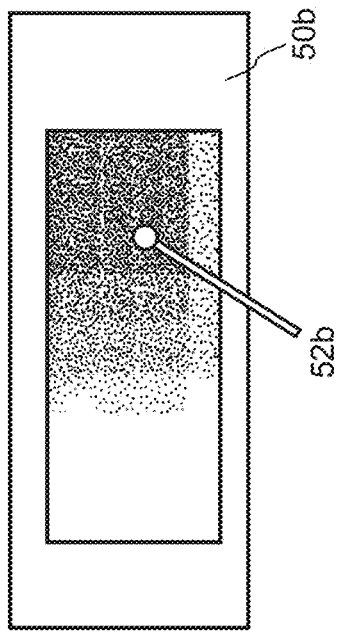
FIGS. 5A, 5B, 5C, and 5D are top plan views of blood smears on slides illustrating how blood smears vary with respect to their length, breadth, and shape.
Figure 5D:
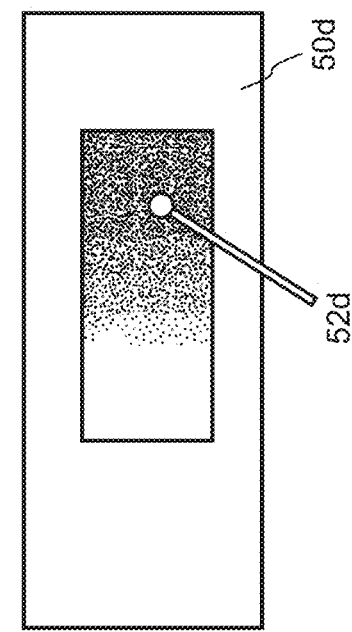
Figure 5A:
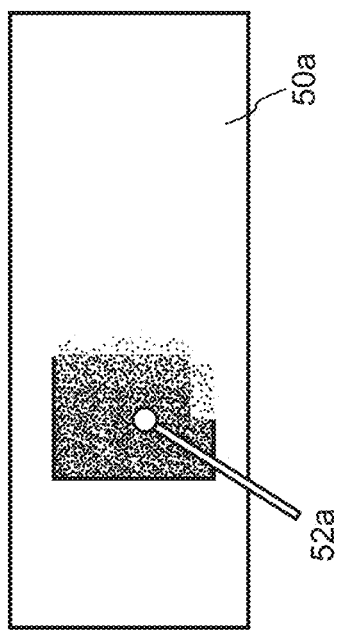
Figure 5C:
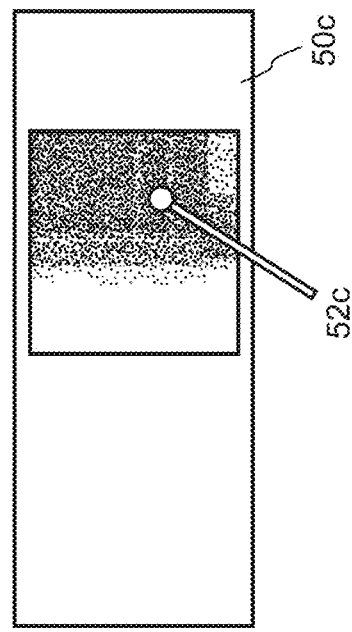

If a spreader by which the cells can be distributed in a monolayer is used, the total area covered by the sample of blood in the blood smear can be determined. The cellular elements in the entire slide can then be counted to provide a complete blood count. Alternatively, the cellular elements in only a portion of the area covered by the monolayer of the sample can be counted, and appropriate calculations can be carried out to determine a complete blood count based on the portion of the entire blood smear that is scanned. FIGS. 1A and 1B illustrate a conventional method for distributing cells in a monolayer.

If a wedge or push approach for creating a blood smear is used, a scan of the optical density or light absorbance of the blood smear can be performed. The value of the optical density or absorbance for a given area of the blood smear is proportional to the thickness of the blood smear along the length and width of the blood smear for that given area. Knowledge of the total optical density of the blood smear can then be used to calculate the volume of the blood contained within the area of the blood smear that can be reviewed reliably. This process addresses the differences between blood smears resulting from differences in overall dimensions of different blood smears, and the areas suitable for morphological review, by recording the value of the optical density measured in a particular portion of the blood smear (e.g., a portion of the total area of the blood smear), comparing that value to the optical density of the entire blood smear (i.e., the total area of the blood smear), and then determining the blood count on the basis of the ratio of the value of the optical density measured in the particular portion of the blood smear (e.g., a portion of the total area of the blood smear) to the optical density of the entire blood smear (i.e., the total area of the blood smear) while accounting for the volume of blood forming the blood smear (i.e., a value that is known or a value that can be determined from the total area of the blood smear). In a given blood smear, the portion of the blood smear that is thick has a higher concentration of hemoglobin than does the portion of the blood smear that is thin. Moreover, the portion of the blood smear that is thick has a higher volume of blood than does the portion of the blood smear that is thin. It would be expected that more white blood cells would be seen per unit area in the thick portion of the blood smear than would be seen per unit area in the thin portion of the blood smear. In other words, if a portion of a given blood smear (i.e., the thick portion) is twice as thick as another portion of the given blood smear (i.e., the thin portion), it would be expected that twice as many white blood cells would be seen in the thick portion of the blood smear as would be seen in the thin portion of the blood smear.

Figure 6A:
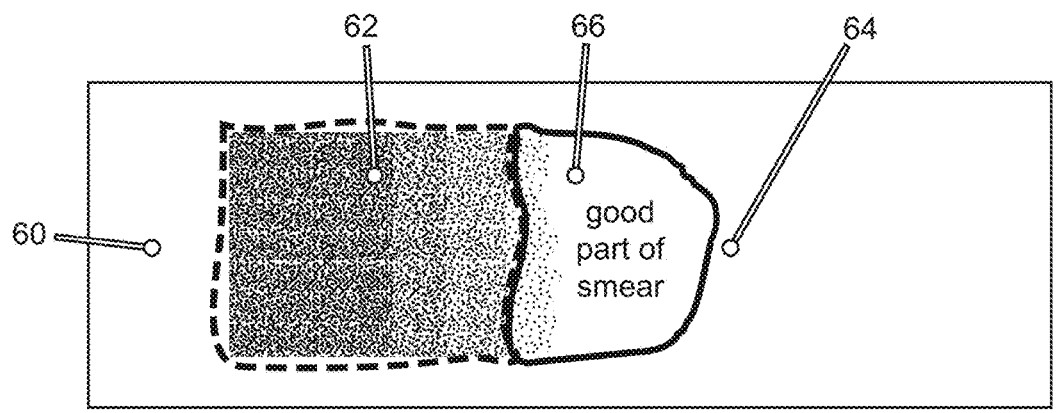
FIGS. 6A, 6B, and 6C are top plan views of a blood smear on a slide illustrating how a low power scan of the optical density of the entire area of a blood smear can be used, in combination with the known volume of the sample of whole blood used to form the blood smear, to calculate the volume of the portion of the sample of whole blood contained within the portion of the blood smear used to carry out the method described herein.
Figure 6B:
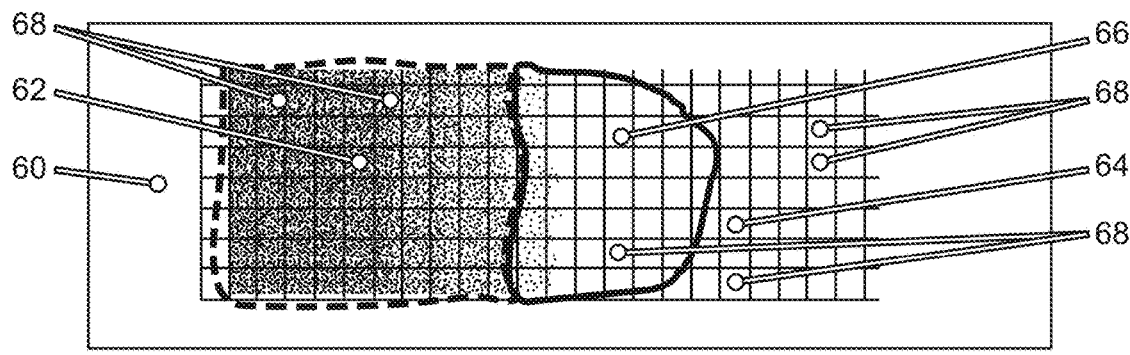
Figure 6C:
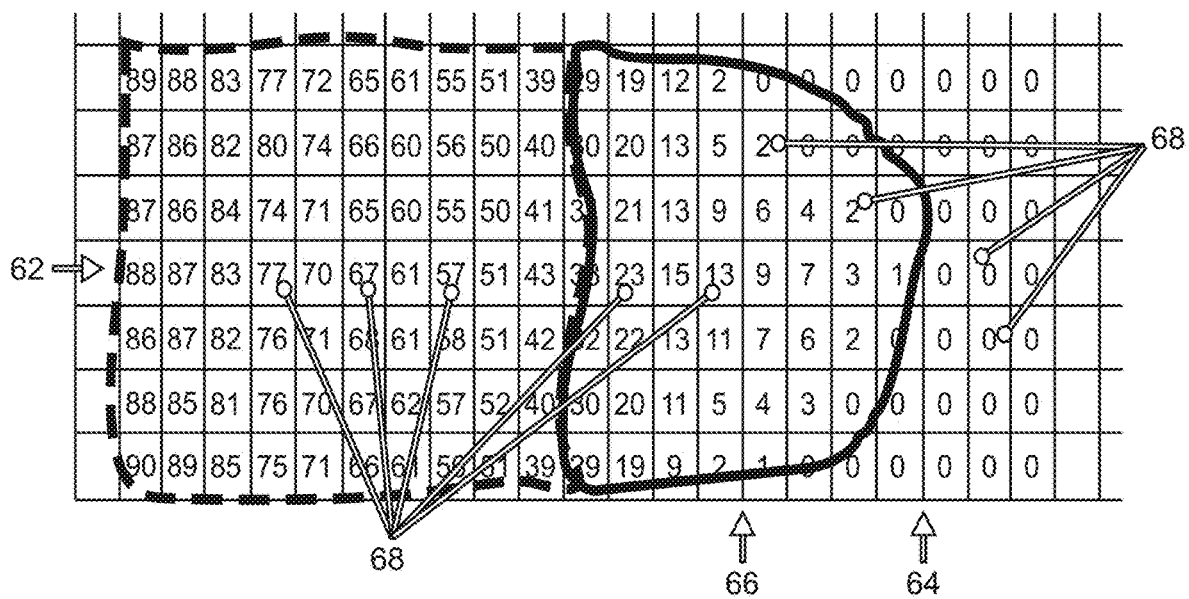

Referring now to FIGS. 6A, 6B, and 6C, which illustrate an example of a blood smear, a slide is designated by the reference numeral 60, the thick portion of the blood smear is designated by the reference numeral 62, the thin portion of the blood smear is designated by the reference numeral 64, and the usable portion of the blood smear is designated by the reference numeral 66. The entire blood smear is divided into smaller sections 68 by means of, for example, a plurality of grid lines parallel to the X-axis and a plurality of grid lines parallel to the Y-axis. A scan of the slide 60 indicates the optical density of each smaller section 68 of the slide 60. A number representing the optical density of each smaller section 68 is imprinted in each smaller section of FIG. 6C. These numbers range from 0 to 90, inclusive. However, these numbers are not measured numbers; they are merely hypothetical numbers. Moreover, these numbers do not actually exist on the slide 60; these numbers merely represent the optical densities of the smaller sections 68. The usable portion of the slide 60 is that portion wherein the values of the measured optical densities of the smaller sections 68 both (a) exceed a low cut-off value and (b) do not exceed a high cut-off value. As shown in FIG. 6C, the low cut-off value is selected to be zero (0) and the high cut-off value is selected to be approximately thirty-eight (38). Therefore, the smaller sections 68 of the usable portion 66 of the slide 60 have optical density values ranging from one (1) to thirty-eight (38), inclusive.

The method and device described herein preferably employ scanning digital microscopy to recognize each of the components in the sample of whole blood. A special class of scanning digital microscopy, digital pathology, is described in greater detail in Digital pathology-Wikipedia, the free encyclopedia, http://en.wikipedia.org/wiki/Digital_pathology, incorporated herein by reference, and the references and links appended thereto. See also Scanning Basics 101—All about digital images, http://www.scantips.com/index-.html, incorporated herein by reference, and the references and links appended thereto, for additional information about scanning digital images. From the value of the volume of sample of whole blood deposited on the slide, the method and device can determine the parameters described below. Total hemoglobin can be determined from the blood smear itself. For example, if two microliters of blood are dispensed to create the blood smear, and the overall measurement of hemoglobin on the slide is 20 g, the absolute volume of blood in a given area of the blood smear can be determined on the basis of the hemoglobin measured in that given area of the blood smear. The number of white blood cells counted in that same given area of the blood smear are counted as cells per unit area and then converted to cells per microliter.

The concentration of hemoglobin can be calculated from the optical density of the entire scanned blood smear. The determination of optical density can be carried out by means of light having a wavelength of 540 nm, which is the maximum absorbance for hemoglobin. However, a different wavelength (or combination of wavelengths) can be used, if so desired. The same scan for determining optical density can be used for selecting red blood cells and measuring their diameter to provide a measurement of mean cell diameter, which can be used as a metameter for cell volume. Variability in the mean cell diameter can be used for assessing variability in the sizes of cells to provide a parameter equivalent to the red cell distribution width. The absorbance of each red cell with respect to hemoglobin content permits derivation of a cell by cell and mean hemoglobin content (mean cell hemoglobin) as well as hemoglobin concentration (mean cell hemoglobin concentration). By measurement of absorbance (or optical density), the concentration of hemoglobin of the entire slide can be determined. The quantity of hemoglobin in each of the red blood cells (or a statistically significant number of the red blood cells) in the desired area for measurement can be measured. This measurement provides the amount of hemoglobin per red blood cell, or hemoglobin content (CH). A mean value can then be calculated (MCH). By having knowledge of the two-dimensional area of each of the red blood cells analyzed, the volumes of the individual red blood cells can be calculated. After the volumes of the individual red blood cells are known, a mean cell volume can be calculated. By using the value of MCH, which is the mean value of the concentration of hemoglobin per red blood cell, and by using the value of MCV, the value of MCHC, which is the average concentration of hemoglobin in a given volume of red blood cells, can be calculated, i.e., MCH/MCV.

The scan of the red blood cells can be used to determine the presence of significant populations of abnormally shaped cells such as sickle cells, red blood cell fragments, tear drop poikilocytes, acanthocytes, echinocytes, and the like. The scans have the capability of recognizing cellular inclusion bodies, such as, for example, Howell-Jolly bodies, malarial parasites, etc. Atypical aggregates of red blood cells, as seen in Rouleaux formation and cold agglutinin disease, can also be detected. Abnormal patterns of hemoglobin distribution can be detected in cases where spherocytes or target cells are present. Fluorochrome stains or supra-vital staining can be used to detect reticulocytes.

With respect to detection of leukocytes, the method and the device described herein can employ the staining properties of leukocytes in the entire blood smear to carry out a count of white blood cells. A smaller area of the blood smear, i.e., that in which the morphological characteristics of the leukocytes can easily be identified, can be used to determine the white blood cell differential and to detect and count nucleated red blood cells. The nucleated red blood cells can be identified on the basis of such features as size, lobularity, granularity (i.e., degree and type of granules), as well as the nuclear and cytoplasmic ratio and morphological characteristics.

Platelets can be counted on the basis of such features as size and uptake of stains. Additionally, interferences in the platelet count caused by satellitism, and, more commonly, aggregation, can also be recognized. Satellitism means an unusual immune reaction that causes platelets to stick to neutrophils. When stained and imaged, the platelets appear to be satellites around the neutrophils. Artifacts resulting from such factors as ageing of the leukocytes in the sample, smear/smudge cells in chronic lymphocytic leukemia, and background staining seen in cases of paraproteinemia, can also be screened. Smear/smudge cells are ruptured chronic lymphocytic leukemia (CLL) cells appearing on the blood smears of CLL patients.

The method and the device described herein can be adapted to use fluorochrome detection, thereby providing access to immunofluorescent staining and uptake of other fluorochrome dyes that can be used for detection of nucleated cells.

Devices capable of performing morphological scanning and recognition of cells have been in existence for several years. See, for example, http://www.cellavision.com/?sid=459, incorporated herein by reference.

The following non-limiting examples illustrated specific techniques for carrying out the method described herein.

Example 1

This example illustrates one approach for using a blood smear technique described herein to carry out a quantitative blood count.

Referring now to FIG. 7, a sample of whole blood 100 drawn from a sample tube "S" and having a known volume is deposited on a microscope slide 110 in an initial drop 120, e.g., 50 microliters. It is assumed that no blood is lost in the process for creating the blood smear. Accordingly, all of the cells in the blood sample are accounted for in the blood smear. The low power imaging device measures optical density or reflectance resulting from the hemoglobin in a piece-wise fashion (i.e., via pixels) across the entire area of the blood smear. The low power imaging device can be a 10× objective lens of a microscope. It is assumed that the optical density or reflectance value of each piece of the image (i.e., pixel) is proportional to the amount of red blood cells in the piece. The term "piece" is synonymous with the smaller section 68, shown in FIGS. 6B and 6C. Thus, a piece (or smaller section 68) having an arbitrary response value of ten (10) optical density units or reflectance units would contain twice as many red blood cells as a piece (or smaller section 68) having a response value of five (5) optical density units or reflectance units, so long as the same method is used to measure each piece (or smaller section 68). The number of measurement units (e.g., optical density units or reflectance units) recorded over the entire area of the blood smear is added to yield a number representing the total quantity of hemoglobin in the blood smear, and, consequently, the total amount of blood in the blood smear is known. For example, the total of all non-zero pixels might add up to 10,000,000 optical density units or reflectance units.

The next step of the volume calculation is to determine which areas of the blood smear are suitable for analysis by means of imaging. The thicker portions of the blood smear contain too many cells for counting. The thicker portions also contain more hemoglobin and therefore would have higher optical density readings or reflectance readings per pixel. An imaging algorithm for low power imaging can be used to determine which areas exhibit an acceptable range for subsequent analysis via high power imaging. For example, it might be empirically determined that areas having pixel values in the range of 1 unit through 38 units, inclusive, represent the correct thickness of the blood smear for counting blood cells, that areas having pixel values of 39 units and greater represent the portion of the blood smear that is too thick for counting blood cells, and that areas having pixel values in the range of less than 1 unit represent the portion of the blood smear that is too thin for counting blood cells. The algorithm would then identify the boundaries of the area of the blood smear where the thickness of the blood smear provides pixel readings in the range of 1 unit through 38 units, inclusive. These boundaries would then be used in the high power imaging step, where only that area within the boundaries is analyzed via high power imaging for the purpose of counting cells.

The pixel reference values of all pixels within the bounded measurement area can be added to obtain a number that is proportional to the total amount of hemoglobin, and, consequently, the total amount of blood, bounded by the measurement area. For example, the total value of all pixels in the area might add up 3,000,000 optical density units or reflectance units. If the total value of all pixels in the entire smear were 10,000,000, from the calculation shown previously, then the area being analyzed represents the fraction of 3,000,000 divided by 10,000,000, which is equivalent to 30% of the total amount of blood, or 0.3 times the total amount of blood in the blood smear. Because it is known that there are 50 microliters of the blood sample in the entire blood smear, the measurement area identified contains 0.3 times 50 microliters, or 15 microliters. This volume is then used at a later point in time when the microscopic imaging system records and counts the various cells in the identified measurement area. Thus, if that system determines that that are 75,000,000 red blood cells in the area identified as being suitable for recording and counting blood cells, the count of red blood cells for that sample of blood would be 75,000,000 per 15 microliters, or 5,000,000 red blood cells per microliter. The same calculation can be used to obtain counts of blood cells per microliter of the blood sample for all other types of cells counted in the measurement area.

In an alternative method of carrying out the method described in this example, if the volume of the whole blood sample applied to the slide is not known, the volume of the whole blood sample applied can be found by means of an independent method of determining the concentration of hemoglobin. For example, if a total of X grams of hemoglobin is measured on the slide by means of measuring optical density units or reflectance units of the blood smear, and if an independent measurement of hemoglobin made by an automated hematology analyzer or a spectrometer indicates that the concentration of hemoglobin is X g/dL, simple mathematics would indicate that the volume of the whole blood sample applied to the slide is 1 dL. Regardless of how the concentration of hemoglobin is measured, once the value of the concentration of hemoglobin is known, the method described herein can be carried out to perform a complete blood count.

Example 2

Figure 8E:
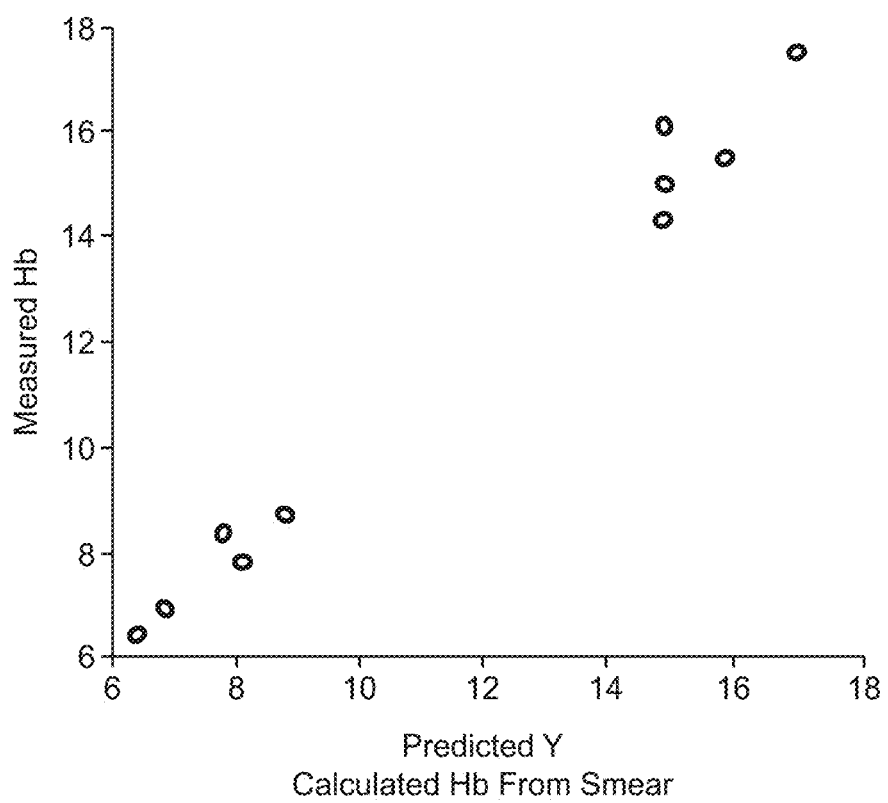
FIG. 8E is a graph illustrating how the determination of optical density by means of scanning is shown to correlate with estimates of hemoglobin concentration made by means of a conventional automated hematology analyzer.

Referring now to FIG. 8A, several different blood smears, ten (10) in number, are shown. These blood smears represent blood smears made with different samples of whole blood containing varying amounts of hemoglobin, which causes the overall optical density or reflectance of the blood smears to differ in intensity. FIG. 8B shows the thick end of each blood smear and the thin end of each blood smear of FIG. 8A. By means of an appropriate scanning procedure, the optical density profile of the blood smear can be graphed. Each point on the X-axis of the graph represents the distance of a point of the blood smear on the slide, as measured from the point of origin of the drop of whole blood on the slide. The Y-axis of the graph represents the optical density or reflectance at a given point of the blood smear on the slide, as measured from the point of origin of the drop of whole blood on the slide. FIG. 8C shows the optical density profiles or reflectance profiles of the blood smears in FIG. 8B. FIG. 8D indicates a general optical density profile or reflectance profile, wherein the area for counting blood cells is distinguished from the area where blood cells are not counted. FIG. 8E illustrates a graph that indicates the correlation between hemoglobin measured by means of an automated hematology analyzer and hemoglobin calculated by scanning a blood smear.

Example 3

This example illustrates a technique for determining a blood count wherein only a narrow portion of the minor axis of the microscope slide is used. Instead of using the approach described in Example 1, the values corresponding to a line of pixels though the center of a slide can be measured by the low power imaging system. It should be noted that the line being scanned has two dimensions, but the minor dimension of the line is much narrower than the minor dimension that is scanned is Example 1. This technique can be used if the device employs a single detection beam through which the slide is moved, i.e., scanned, while the optical density values or reflectance values are recorded. While not being a true imaging system, the same result is produced by scanning a line rather than the plurality of lines needed to make up a larger area. It is believed that this embodiment is less expensive that the embodiment described previously.

If the pixel values along the line being scanned, e.g., reflectance or optical density, are plotted as a function of the position at which the measurement is made, graphs in the center of the slide are obtained. The abscissa (X-axis) represents the linear position or distance on the line through the middle of the blood smear, and the ordinate (Y-axis) represents the relative optical density or reflectance units measured at that linear position on the line. The profile on the graph can then be used to identify the point at which the blood smear becomes sufficiently thin to allow recording and counting blood cells by the high power imaging system. The point on the profile at which the measurements of reflectance drop below a certain value is the point at which the boundary for the identified measurement area is set. This point is referred to herein as the cut-off point. That information is then transmitted to the high power imaging system, which then only records and counts cells in the area of the blood smear set by that boundary. In other words, the "area reviewed" on the slide is the area bounded at the leading edge by a line across the slide, perpendicular to the line by which the measured profile was obtained. The perpendicular line across the slide passes through the point identified as the cut-off point. All points on the blood smear that are downstream (i.e., those that are in the thinner portion of the blood smear) in the blood smear are recorded and counted.

The volume of the area recorded and the position where blood cells are counted is calculated in a manner that is analogous to that employed in the embodiment described previously. All the pixel reflectance measurements on the scanned line are added, i.e., integrated, to obtain a number representing the total amount of hemoglobin in the blood smear. The quantity of blood in the blood smear can be derived from the total amount of hemoglobin in the blood smear. The same types of measurements and calculations as were used in the embodiment described in Example 1 are carried out for all points on the profile in the area identified for review. Again, the proportion of blood from the original sample designated by the reviewed areas is determined by recording the value of the optical density measured in a particular portion of the blood smear (e.g., a portion of the total area of the blood smear), comparing that value to the optical density of the entire blood smear (i.e., the total area of the blood smear), and then determining the blood count on the basis of the ratio of the value of the optical density measured in the particular portion of the blood smear (e.g., a portion of the total area of the blood smear) to the optical density of the entire blood smear (i.e., the total area of the blood smear) while accounting for the volume of blood forming the blood smear (i.e., a value that is known or a value that can be determined from the total area of the blood smear). The assumption made for this embodiment is that the thickness of the blood smear is uniform along the minor axis of the slide, that is, the dimension perpendicular to the scanned line used by the low power imaging system to measure the profile. Any asymmetry or uniformity along this axis would introduce error in the determination of volume derived from the single axis line through the blood smear.

The method and the device described herein can consolidate the process of blood counting and review of a blood smear in a single instrument. The method and device require only a few reagents, which reagents are inexpensive. The method and device are not complex in a technological sense, because only a single undiluted volume of whole blood is used.

Interfering materials, such as, for example, lyse-resistant red blood cells, would not be a problem. The disposable component is single glass slide. The device is capable of storing its output as an electronic image. The optics can be arranged to permit fluorescence detection. The volume of sample required would be very low.

Because all of the sample would be used for the analysis, the precision will be high, particularly when samples of body fluid, more particularly, samples of blood, are analyzed. Control materials can be limited to use of reference smears. The method and device described herein can detect abnormalities that are currently undetectable by conventional hematology analyzers. Such abnormalities include abnormal red blood cell associations (Rouleaux and aggregation), red blood cell inclusion bodies such as Howell-Jolly bodies and malarial parasites. The method and device described herein can also show sub-cellular changes in the white blood cells, such as the Auer rods seen in acute myeloid leukemias or nucleoli seen in blast cells. Finally, the method and device described herein can detect plasma abnormalities, such as, for example, increases in protein levels, which can be seen in cases of paraproteinemia.

The analysis of the blood cell count and the blood smear can be performed on the same blood sample, thereby giving the user the opportunity to directly review the instrument's interpretation of the classification of cells.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining an analysis area of a blood smear, the method comprising:
    measuring an absorbance or a reflectance value of light attributable to hemoglobin in a plurality of red blood cells in a plurality of sections of the blood smear to determine a pixel value for each of the plurality of sections of the blood smear; and
    identifying as an analysis area of the blood smear a section of the blood smear that has a pixel value within a predetermined range;
    wherein the pixel value is optical density.

2. The method of claim 1, comprising fixing and staining the dried blood smear prior to the measuring step.

3. The method of claim 1, comprising identifying as the analysis area of the blood smear a section of the blood smear that has the optical density between 0 and 38.

4. The method of claim 1, wherein the analysis area of the portion of the blood smear has a thickness that is below an upper cut-off value and above a lower cut-off value.

5. The method of claim 1, wherein the volume of the sample of whole blood is known.

6. The method of claim 5, further comprising counting the blood cells in the analysis area.

7. The method of claim 6, wherein the blood cells counted in the analysis area comprise white blood cells.

8. The method of claim 6, wherein the blood cells counted in the analysis area comprise platelets.

9. The method of claim 6, wherein the blood cells counted in the analysis area comprise red blood cells.

10. The method of claim 6, comprising determining a complete blood count from the analysis area of the blood smear.

\* \* \* \* \*